US006407212B1

(12) United States Patent
Morgenthaler et al.

(10) Patent No.: US 6,407,212 B1
(45) Date of Patent: Jun. 18, 2002

(54) METHOD FOR THE REMOVAL OF CAUSATIVE AGENT(S) OF TRANSMISSIBLE SPONGIFORM ENCEPHALOPATHIES FROM PROTEIN SOLUTIONS

(75) Inventors: Jean-Jacques Morgenthaler, Boll; Jacques-Andre Maring, Münchenbuchsee; Markus Rentsch, Burgdorf, all of (CH)

(73) Assignee: ZLB Bioplasma AG, Bern (CH)

( * ) Notice: Subject to any disclaimer, the term of this patent is extended or adjusted under 35 U.S.C. 154(b) by 0 days.

(21) Appl. No.: 09/582,644

(22) PCT Filed: Dec. 14, 1998

(86) PCT No.: PCT/EP98/08166

§ 371 (c)(1),
(2), (4) Date: Jul. 28, 2000

(87) PCT Pub. No.: WO99/41274

PCT Pub. Date: Aug. 19, 1999

(30) Foreign Application Priority Data

Feb. 11, 1998 (EP) .............................................. 98810108

(51) Int. Cl.[7] .......................... B01D 15/00; C07K 1/14; C07K 14/47

(52) U.S. Cl. ...................... 530/380; 210/661; 210/691; 210/692; 530/415; 604/5.02

(58) Field of Search ................................. 210/661, 679, 210/691, 692, 905; 530/363, 364, 380, 381, 382, 383, 384, 385, 386, 390.1, 390.5, 412, 415, 417, 427; 604/4.01, 5.01, 5.02, 5.03, 5.04, 7

(56) References Cited

U.S. PATENT DOCUMENTS 5,696,236 A 12/1997 Omar et al. ................ 530/380
6,221,614 B1 * 4/2001 Prusiner et al. ............. 435/7.1

FOREIGN PATENT DOCUMENTS

EP            0416983 A1    3/1991
WO            WO97/34642    9/1997
WO            WO98/00441    1/1998

OTHER PUBLICATIONS

P.L. Lantos, Histopathology, vol. 20, No. 1, "From slow virus to prion: a review of . . . ", pp. 1–11, Jan. 1, 1992.
Walker et al, Jour. of Chromatography, vol. 680, No. 1/02, "Aqueous two–phase partition . . . ", pp. 91–96, May 1996.
Heye et al, The Lancet, vol. 343, "Creutzfeldt–Jakob disease and blood transfusion", pp. 298–299, Jan. 29, 1994.
Esmonde et al, The Lancet, vol. 341, "Creutzfeldt–Jakob disease and blood transfusion", pp. 205–207, Jan. 23, 1993.

* cited by examiner

Primary Examiner—Jeffrey E. Russel
(74) Attorney, Agent, or Firm—Jacobson Holman, PLLC

(57) ABSTRACT

For separating non-conventional transmissible agents (NCTAs), i.e. causative agent(s), of transmissible spongiform encephalopathies (TSEs) from a solution of a protein susceptible to contamination with NCTAs, particularly from blood products, at least one adsorbent is suspended, for a time of at least 10 minutes. The absorbent is selected from kieselguhr, diatomaceous earth, silicic acid, clay minerals, metal hydroxide, metal oxihydrate, cellulose, perlite, bentonite, and water-insoluble synthetic polymers. The obtained suspension is agitated, and subsequently the adsorbent is separated from the protein solution.

18 Claims, 1 Drawing Sheet

METHOD FOR THE REMOVAL OF CAUSATIVE AGENT(S) OF TRANSMISSIBLE SPONGIFORM ENCEPHALOPATHIES FROM PROTEIN SOLUTIONS

The present invention concerns a method for the removal of the causative agent(s) of transmissible spongiform encephalopathies (TSEs) from protein solutions, particularly from blood products that will be used for therapeutic and other medical purposes. The protein solution is brought into contact with an adsorbent to which the agent(s) will be bound.

In world war II a method was developed in the USA for the isolation of proteins from human blood plasma. These isolated proteins are used medically as therapeutic agents. Albumin, immunoglobulins, fibrinogen, coagulation factors and numerous other proteins are examples of products of this method. Albumin is used, e.g., for bum patients or more generally in diseases in which the blood volume has to be increased. Immunoglobulins may be used in patients who are not able to synthesize protective antibodies themselves. Coagulation factor concentrates (in particular factor VIII and factor IX) are being used for hemophilia patients. In many cases these preparations are life-saving and therefore they have no substitute.

The methods for the separation of blood plasma in individual proteins are based on several different principles. The older methods which are still being used on a large scale are based on fractional precipitation of the proteins with ethanol and subsequent separation of the phases by centrifugation or filtration. In newer fractionation schemes, other separation methods are used as well, e.g., ion exchange chromatography or (immune) affinity chromatography. An integrated separation scheme usually comprises several different methods which are combined in an optimized process.

In the first years of use of plasma proteins in humans it became clear that products made from human blood also have disadvantages: they may transmit some infectious diseases which are caused by viruses. The most important virus in the beginning was viral hepatitis (hepatitis B). Later on other forms of hepatitis became known (non-A non-B hepatitis which was recently identified and named hepatitis C). The best known virus which is transmitted by blood and blood products is the HIV (Human Immunodeficiency Virus), the causative agent of AIDS (Acquired Immune Deficiency Syndrome). Apart from those mentioned so far, there are some other viruses that may also be transmitted by plasma and plasma derivatives.

In recent years other transmissible diseases with some common features became known. They are called TSEs and believed to be transmitted by non-conventional transmissible agents (NCTA). The human diseases Creutzfeldt-Jakob disease (CJD), Gerstmann-Sträussler-Scheinker disease (GSS), fatal familial insomnia (FFI), and kuru all belong in this group, as do some animal diseases, the best known of which are scrapie in sheep and bovine spongiform encephalopathy (BSE; "mad cow disease") in cattle. Affected humans and animals all show symptoms of neurodegeneration and the diseases are invariably fatal. CJD, the best known human disease in this group, most often develops sporadically; in some cases, however, clustering in certain families was observed latrogenic transmissions through pituitary gland extracts, contaminated instruments used in neurosurgical procedures, and transplantation of cornea or dura mater has also been described. A transmission of any of the human diseases by blood transfusion has never been shown. A retrospective epidemiological study among recipients of transfused blood did not show an increased rate of CJD when compared with non-transfused controls [T. F. G. Esmonde, R. G. Will, J. M. Slattery et al.: Creutzfeldt-Jakob disease and blood transfusion. Lancet 1993, 341: 205–207]. A look-back among recipients of erythrocyte concentrates donated by a man who later on died of confirmed CJD did not show a single case of abnormal neurological or psychiatric findings [N. Heye, S. Hensen, N. Müller: Creutzfeldt-Jakob disease and blood transfusion. Lancet 1994, 343: 298–299]. Transmission of TSEs by blood transfusion must therefore be either extremely rare or extremely inefficient or both. The public and the regulatory authorities are nevertheless aware of a potential problem, and need reassurance that utmost care is exercised to protect the patients from a possible exposure to NCTAs.

The existence of an infectious agent is proven beyond the shadow of a doubt. The exact nature of this agent is, however, still debated. In the past, most researchers believed the disease to be caused by a slow virus; the more popular hypothesis now is that the infectious agent is a proteinaceous particle which may or may not contain nucleic acid, a so-called prion. Prions occur in at least two different forms, one normally found in cells which is called $PrP^c$, and another form which only occurs in individuals affected by the disease which is called $PrP^{sc\ or\ PrPres}$ for its association with scrapie or for its resistance to degradation by proteases, most notably protease K. The difference between $PrP^c$ and $PrP^{res}$ is brought about by changes in folding, or tertiary structure, of the protein, a predominantly α-helical conformation being changed mostly to β-sheets. $PrP^{res}$ is associated with, or may be the cause of, the TSEs. The involvement of other factors (cofactors, i.e., nucleic acids, other proteins) is also being discussed.

The safety of blood and blood derivatives may be increased by 5 measures taken on different levels: (1) the collecting agencies try to exclude donors who are known to pose a high risk for transmitting infectious diseases. This is done with the aid of a questionnaire which allows exclusion of people with increased risk factors. Persons with increased risk factors are, e.g., those who suffer from certain diseases, those who visited certain countries shortly before donation, those who incur risks through their sexual activity or drug addicts who use contaminated needles, recipients of corneal or dura mater transplants, people who have been treated with pituitary hormones or whohave CJD-cases in their family. (2) Laboratory analyses allow the determination of infectious donations which can then be removed from further processing. Those two measures taken together result in removal of most infectious donations but not all: (a) the sensitivity of the test methods may be insufficient; (b) a test for a particular infectious agent may not yet be available; for practical and economic reasons it is not possible to screen for all potential infectious agents; (c) the test does not detect the infectious agent itself, but rather the antibodies that are elicited in the infected person as a response to the infection. From the time of infection until detectable antibodies appear, usually a few days or weeks elapse (so called window). Antibody tests are useless during this period; (d) an infected donation may be released because of a clerical error. (3) The safety with respect to transmission of infectious agents is further improved by special steps that are introduced into the production process which either inactivate or eliminate infectious agents. (4) Strict adherence to good manufacturing practice (GMP) guarantees the efficiency of the steps mentioned under (3). (5) Full traceability of every donation to the corresponding products and from the final products back to the individual donation allows directed recalls of products, should this become necessary.

Methods for detection, inactivation, and elimination of infectious viruses in blood and plasma products are now widely established. Commercial detection systems are used world-wide for detecting, e.g., antibodies to human immunodeficiency virus or to hepatitis C virus. Inactivation of viruses may be achieved by various heat treatments (either in solution or in the dry state; at different temperatures and for different periods of time), by chemical (with a combination of solvents and detergents or with iodine), or photochemical treatments (e.g., exposure to β-propiolactone and ultraviolet light; illumination of a protein solution to which a suitable dye has been added), or by any of many other well known methods. New methods are still being developed. Transmission of known viruses by pharmaceuticals produced from human plasma can nowadays be ruled out with almost complete certainty, transmission of unknown viruses is at least highly unlikely.

The situation is, unfortunately, more difficult with NCTAs. Blood donors are routinely asked questions aimed at eliminating those with an increased risk of contracting CJD later in their life (have family members ever suffered from CJD or similar diseases? Has the donor ever been exposed to pituitary hormones or to a corneal/dura mater transplant?). There is no doubt that this line of questioning may eliminate some of the potential iatrogenic and familial cases, but it will not affect the potential sporadic cases. Elimination of high-risk donors by questioning is therefore at best haphazard, and it is predictable that many cases will slip through. Screening of the donations is not yet possible. Although monoclonal antibodies have been developed which recognize PrP, most do not distinguish between $PrP^c$ and $PrP^{res}$; the assay would therefore have to incorporate a protease digestion, which makes it too cumbersome for routine use. Even worse, it is not at all sure whether $PrP^{res}$ is to be found in blood or plasma; the better source for a tissue specimen would be a brain biopsy, which is clearly not possible with blood donors. It might be possible to develop an assay based on a newly described monoclonal antibody which reacts specifically with $PrP^{res}$ [Korth et al.: Prion ($PrP^{Sc}$)-specific epitope defined by a monoclonal antibody. Nature 1997, 390: 74–77]; however, this has not yet been done.

Unfortunately, the agent(s) of TSE are uncommonly stable against inactivation. The methods mentioned above for the inactivation of viruses do not diminish the infectivity of NCTAs. As a matter of fact, they even survive autoclaving (steam treatment at 121° C. for 15 min) and burial in the ground for several years. Few conditions are known to reliably inactivate NCTAs: autoclaving at increased temperature ($\geq 134°$ C. for at least 18 min; treatment with 1 Mol/L of sodium hydroxide solution, preferably at elevated temperatures; strongly oxidizing conditions (sodium hypochlorite); strongly chaotropic conditions (guanidinium isothiocyanate). If such conditions were used on a solution of human plasma proteins, the proteins themselves would be inactivated at least as rapidly as the NCTAs. The only alternative appears to be physical removal of the NCTAs. Since the monomers of the infectious compound(s) may be of similar size as human plasma proteins, they cannot easily be removed by, e.g., (nano)filtration or centrifugation. It has indeed been shown that nanofiltration was able to remove NCTAs, but that the removal depended on the presence or absence of certain solutes; e.g., the infectious agents passed through the filter in the presence of surfactants.

Companies that process human blood or blood plasma therefore have the need for industrially applicable methods that allow a safe removal of NCTAs from protein solutions. In order to minimize the theoretical risk of infection for the patients who are treated with such products, it is thus the aim of the present invention to describe a method which allows the separation of NCTAs from protein solutions on an industrial scale; this method may be part of any current plasma fractionation scheme.

The object of the present invention is therefore to provide a method for a safe removal of NCTAs from solutions of protein susceptible to contamination with NCTAs.

It was found that NCTAs which may be present in protein solutions adsorb on certain materials e.g. modified cellulose, diatomaceous earth, bentonites, volcanic earth, particles of artificial polymers etc. If the protein solutions are brought in contact with these materials for a sufficiently long time, the separation of a solution into a precipitate and a supernatant therefore results in further removal of NCTAs in addition to the removal effected by the precipitation step per se. The materials mentioned above have been introduced earlier into plasma fractionation as so-called filter aids in order to facilitate the separation of the precipitate and the supernatant during ethanol fractionation. The filter aids form a layer on top of the porous filter membranes and they promote filtration because they are permeable for liquid but not for solid particles. The filter aids prevent the clogging of the filter pores by small proteinaceous particles.

Removal of different viruses from protein solution by a similar method has been described in an earlier patent (EP 0 679 405 A1). In view of the fact that the nature of the NCTAs is, as mentioned above, still debated, it was not at all obvious that they should behave like viruses.

According to the present invention, NCTAs are removed from a protein solution by adsorption on a solid phase, said solid phase being either suspended in solution in order to adsorb the NCTAs or having already been formed beforehand on a porous filter. The protein solution has to be brought into contact at least once with an adsorbent chosen from the group kieselguhr, diatomaceous earths, silicic acid, clay minerals, metal hydroxide or -oxihydrate, cellulose, perlite, and water insoluble synthetic polymers, or a mixture or combination of these materials; contact time is at least 10 min. Subsequently, the suspension is separated into supernatant and precipitate by filtration or any other suitable method.

Solid phases for this technology are, e.g., the filter aids Celite™ (Johns-Manville Corp.) Aerosil® (Degussa), perlite, heat expanded perlite, bentonite, or in general finely distributed solids which can be removed by filtration or centrifugation from a suspension. Substances like metal hydroxide gels (e.g. Alhydrogel $Al(OH)_3$ as a gel in water) are also suitable.

The adsorption of NCTAs on the materials mentioned depends on the material used, the NCTA, and the environment. By systematic change of the environment, the "stickiness" of a particular NCTA onto the same material may be changed. It may be possible to modify the adsorption of NCTAs to a particular material by, e.g., changing the pH-value of the medium. Other solution parameters like temperature, ionic strength, salts, and organic solvents may also influence the adsorption of NCTAs and may be used in order to improve adsorption and therefore the removal of NCTAs from the protein solution.

Even a short treatment of the protein solution for only 10 minutes can result in a substantial removal of NCTAs. It may, however, be advantageous to treat for a longer time in order to improve removal of NCTAs. Treatment times may be approximately 15 min, 30 min, approx. 1 h, approx. 2 h, approx. 6 h, approx. 8 h, approx. 12 h, ca approx. 14 h, approx. 16 h, approx. 20 h.

The removal of the adsorbent including the adsorbed NCTAs is done either by centrifugation or filtration. Centrifugation may be done in different ways, e.g., by a batch procedure or a continuous centrifugation. Centrifugal force and time of centrifugation have to be adjusted so that a clean separation of suspended material and supernatant is guaranteed. On a laboratory scale, filtration may be carried out with a Büchner funnel or a similar apparatus. On larger scale (production) other equipment is preferred, e.g., filter presses or rotating filters.

EXPERIMENTAL

For obvious reasons, it is not possible to conduct experiments with the causative agent(s) of CJD or similar human diseases in man. In order to learn something about the behavior of NCTAs it is therefore necessary to resort to model systems. One well established model system is a hamster scrapie model. The following is a brief description of the model: First, an inoculum is prepared from the brain of a diseased animal; the brain is removed carefully and homogenized by sonication with 9 volumes of phosphate buffered saline. This preparation can transmit the disease when 50 µL are inoculated intracranially into healthy hamsters. Depending on the potency of the inoculum, disease will develop within a few weeks or several months. All animals have to be observed for a year or until they die, whichever comes first. The disease manifests itself by characteristic behavioral changes, e.g., increased response to noise and ataxia. By diluting the inoculum in steps of 1 in 10 with buffer and inoculating the dilutions into animals, it is possible to define a titer of the inoculum; the titer is the reciprocal of the last dilution which caused disease in half the animals that were inoculated. An inoculum prepared as described above has a titer of about $10^{12}$. The advantage of this model is that it does not make any assumptions concerning the nature of the infectious agent(s), since the assay relies on clinical disease. The infectious agent(s) may therefore be one or more proteins, with or without nucleic acid(s) involved, a slow virus or any other entity, it is always the infectious agent(s) which are measured. This system may therefore be used to assess either the physical removal or the inactivation of the causative agent(s) of TSEs. Experiments are carried out in analogy to validation experiments with viruses, which have been described in detail in the literature for the past approximately ten years: a small amount of the infectious material (the so-called spike) is added at a particular step of the purification process of the product under evaluation and its activity is measured. The next process step is then performed (e.g., a precipitation, followed by separation of precipitate and supernatant; a thermal inactivation) and the remaining activity is titrated, in both phases in the case of physical separation, or as a function of time in the case of inactivation. Inactivation factors can be calculated from these measurements, provided the balance sheet tallies or the kinetics were followed correctly. In the case of NCTAs titration is extremely cumbersome, because every titration point requires the use of several animals; the protocols have therefore to be amended accordingly. The outcome of the experiments is only known after several months, when the infected animals will either have contracted the disease or remained healthy.

EXAMPLES

The brain homogenate used in all the following examples was carefully titrated by injecting dilutions into hamster brains. After 187 days of observation, the distribution of sick and healthy animals in the different cohorts was as follows:

| dilution | challenge 1 | challenge 2 |
| --- | --- | --- |
| $10^{-1}$ | 4/4 | 4/4 |
| $10^{-2}$ | 4/4 | 4/4 |
| $10^{-3}$ | 4/4 | 4/4 |
| $10^{-4}$ | 4/4 | 3/3 |
| $10^{-5}$ | 4/4 | 4/4 |
| $10^{-6}$ | 4/4 | 4/4 |
| $10^{-7}$ | 4/4 | 3/4 |
| $10^{-8}$ | 5/8 | 6/8 |
| $10^{-9}$ | 3/8 | 2/8 |
| $10^{-10}$ | 0/4 | 1/4 |
| $10^{-11}$ | 0/4 | 0/4 |

From these data, a titer of approximately $10^9$ can be calculated for the homogenate. Similar tables were generated for each of the solutions analyzed. From these data, clearance factors for each example were calculated; they are indicated with each example.

Example 1

Figure 1:
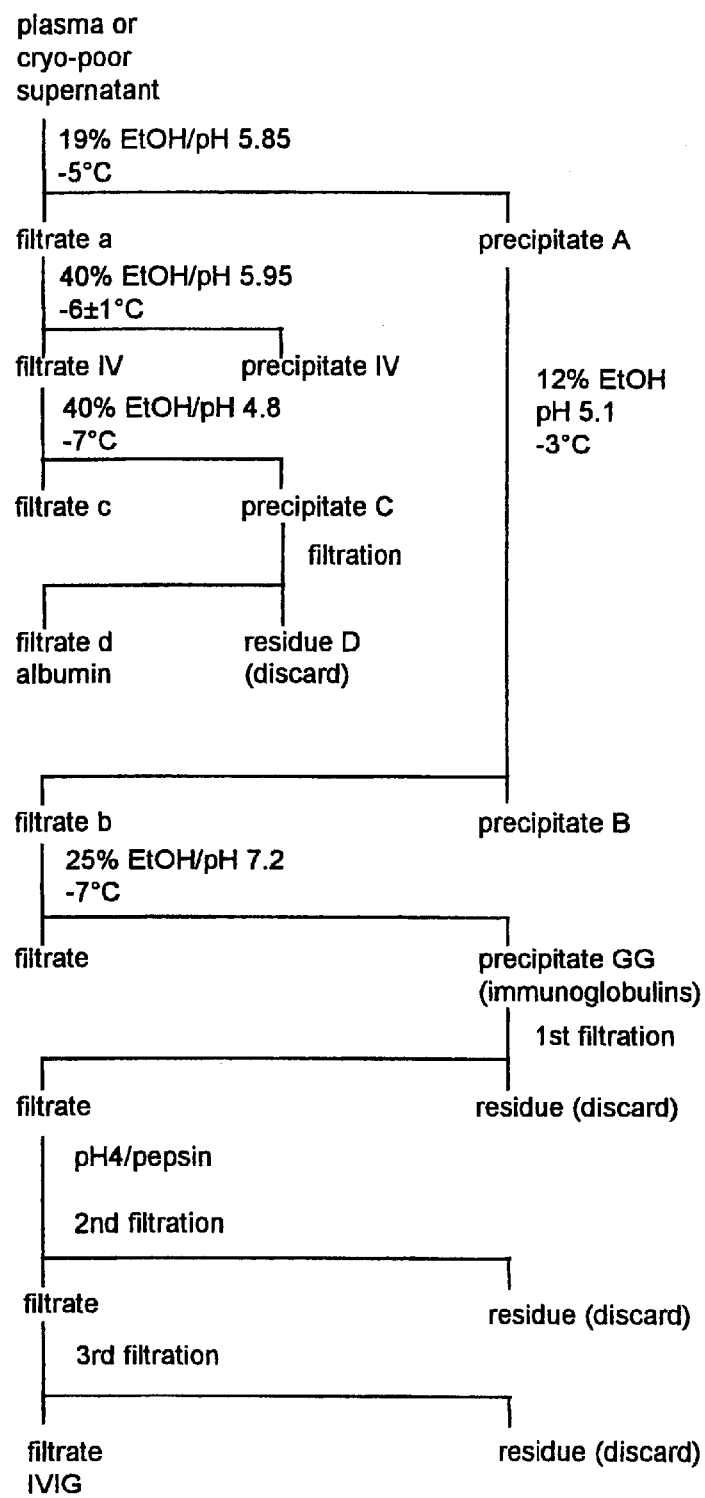
FIG. 1 shows a diagram of the plasma fractionation method according to Kistler/Nitschmann from which method some fractions were used as test material in the examples.

(For this and the Following Examples, Refer Also to FIG. 1 Showing a Diagram of the Plasma Fractionation Method According to Kistler/Nitschmann)

58 ml of human blood plasma were stirred and cooled to 1° C. 0.58 ml of brain homogenate was added. Ethanol was added to a final concentration of 19% with concomitant cooling of the plasma to −5.5° C. After adjustment of the pH to 5.8 perlite was added, and the suspension was centrifuged. The infectivity in the supernatant was reduced by a factor of $\approx 10^5$.

Example 2

40 ml of filtrate a were stirred at −5.5° C. 0.4 ml of brain homogenate was added, followed by addition of ethanol to a final concentration of 40%. Temperature was decreased to −7° C. and the pH was adjusted to 5.95. A mixture of perlite and Celite™ was added. The suspension was centrifuged. The infectivity in the supernatant was reduced by a factor of $\approx 10^5$.

Example 3

52 mL of precipitate A were stirred at 1° C. 0.52 ml of brain homogenate was added. Buffer was added and the pH adjusted to 5.1. Water was added, then ethanol to a final concentration of 25%. Temperature was reduced concomitantly to −3° C. Perlite was added and the suspension was centrifuged. The infectivity in the supernatant was reduced by a factor of $\approx 10^6$.

Example 4

33 ml of re-suspended precipitate GG (which contains filter aid from the previous step) were cooled to 4° C. 0.33 ml of brain homogenate was added. The suspension was centrifuged. The infectivity in the supernatant was reduced by a factor of $\approx 10^7$.

Example 5

50 ml of immunoglobulin G solution were stirred at 4° C. 0.5 mL of brain homogenate was added, followed by filter aid (Celite™ 577). The suspension was centrifuged. The infectivity in the supernatant was reduced by a factor of $\approx 10^6$.

Example 6

33 ml of re-suspended precipitate GG were cooled to 4° C. and spiked as described in Example 4. The suspension was centrifuged and the supernatant further treated as in Example 5 (addition of filter aid, followed by centrifugation; volumes adjusted accordingly), but without an additional spike with brain homogenate. After over 200 days of observation, none of the animals injected with the second supernatant showed any signs of disease. This demonstrates that twofold filtration in sequence in the presence of suitable filter aids removes substantially more of the infectious agent(s) than any single filtration would.

What is claimed is:

1. A method for separating causative agents of transmissible spongiform encephalopathies which comprises suspending at least one absorbent selected from the group consisting of kieselguhr, diatomaceous earth, silicic acid, clay minerals, metal hydroxide, metal oxihydrate, cellulose, perlite, bentonite, and water insoluble synthetic polymers in a solution of a protein susceptible to contamination with the causative agents for a time of at least 10 minutes during which the obtained suspension is agitated, and subsequently separating the absorbent from the protein solution.

2. The method according to claim 1, wherein the absorbent is separated from the solution of a protein susceptible to contamination with the causative agents by centrifugation or filtration.

3. The method according to claim 1, wherein the solution of a protein susceptible to contamination with the causative agents is a preparation based on human blood plasma.

4. The method according to claim 1, wherein the adsorbent is an insoluble metal hydroxide or metal oxihydrate.

5. The method according to claim 4, wherein the adsorbent is magnesium or aluminum hydroxide.

6. The method according to claim 1, wherein the adsorbent contains aluminum hydroxide gel or cellulose.

7. The method according to claim 1, wherein the adsorbent is diatomaceous earth, perlite, heat expanded perlite, bentonite, or talcum.

8. The method according to claim 1, wherein the adsorbent is present in the form of a gel.

9. The method according to claim 1, wherein the solution of a protein is susceptible to contamination with the causative agents is contacted at least twice with a fresh portion of the absorbent.

10. The method of claim 9 wherein the solution is contacted three times with a fresh portion of the adsorbent.

11. The method of one of claim 1, wherein the pH of the suspension is within the range of 4 to 7.

12. The method of claim 1, wherein one or more of the parameters of the solution are changed at least once during the contact time of the solution with the adsorbent.

13. The method of claim 12, wherein the parameters of the solution are the temperature, the concentration of one or more solutes and the ionic strength.

14. The method of claim 1, wherein the solution of the protein susceptible to contamination with the causative agents is contacted with the absorbent for 10 minutes to 48 hours.

15. The method of claim 1, wherein the temperature of the protein solution is within the range of 0° C. to 20° C.

16. The method of claim 1, wherein the solution of the protein susceptible to contamination with the causative agents is contacted with the absorbent for 30 minutes to 12 hours.

17. The method of claim 1, wherein the solution of the protein susceptible to contamination with the causative agents is contacted with the absorbent for 3 to 48 hours.

18. The method of claim 1, wherein the temperature of the protein solution is about 2° C.

* * * * *